United States Patent [19]

Baldwin et al.

[11] 4,144,343

[45] Mar. 13, 1979

[54] HETEROCYCLE SUBSTITUTED (3-LOWERALKYLAMINO-2-R₁O-PROPOXY)PYRIDINES

[75] Inventors: John J. Baldwin; Gerald S. Ponticello, both of Lansdale, Pa.

[73] Assignee: Merck & Co., Inc., Rahway, N.J.

[21] Appl. No.: 866,962

[22] Filed: Jan. 4, 1978

[51] Int. Cl.² .................. A61K 33/44; C07D 403/02; C07D 413/02
[52] U.S. Cl. ................................... 424/263; 546/277; 546/281; 546/316
[58] Field of Search ............. 260/296 AE, 294.8 R; 424/263

[56]  References Cited
U.S. PATENT DOCUMENTS

| 3,946,009 | 3/1967 | Wasson et al. | 260/250 BN X |
| 4,000,282 | 12/1976 | Baldwin | 424/263 |
| 4,060,601 | 11/1977 | Baldwin | 424/263 |
| 4,065,461 | 12/1977 | Ross-Petersen | 260/296 AE |

FOREIGN PATENT DOCUMENTS 1405946  3/1977  United Kingdom ............ 260/296 AE

*Primary Examiner*—John D. Randolph
*Attorney, Agent, or Firm*—Daniel T. Szura; Harry E. Westlake, Jr.

[57]  ABSTRACT

Heterocycle substituted (3-loweralkylamino-2-R₁O-propoxy)pyridines, their pharmaceutically acceptable salts and their preparation are disclosed. These pyridines have pharmaceutical properties such as antihypertensive activity of rapid onset.

19 Claims, No Drawings

HETEROCYCLE SUBSTITUTED (3-LOWERALKYLAMINO-2-$R_1$O-PROPOXY)PYRIDINES

BACKGROUND OF THE INVENTION

The present invention concerns heterocycle substituted-(3-loweralkylamino-2-$R_1$O-propoxy)pyridines having pharmaceutically useful properties.

Hypertension in man and other animals can be treated with various chemical agents. One such class of agents is that known as the $\beta$-adrenertic blocking agents or $\beta$-blockers. While this class of agents can have antihypertensive activity, the onset of this activity is generally gradual. The structure and activity of $\beta$-blockers is generally discussed in "Clinical Pharmacology and Therapeutics" 10, 252, 306 (1969). Substituted carbocyclic aryl $\beta$-adrenergic blocking agents are disclosed in British Pat. No. 1,206,420, British Pat. No. 1,304,303, U.S. Pat. Nos. 3,644,636 and 3,459,782. Substituted N-heteroaryl $\beta$-adrenergic blocking agents are disclosed in British Pat. No. 1,305,644, U.S. Pat. Nos. 4,000,282, 3,946,009, Journal of Medicinal Chemistry 16, 113-114 (1973) and Journal of Medicinal Chemistry 15, 1321 (1972).

Another class of anti-hypertensive agents are the vasodilators. Vasodilators, however, normally cause undersirable tachychardia.

Heterocycle substituted (3-loweralkylamino-2-$R_1$O-propoxy)pyridines have been discovered. These compounds have antihypertensive activity of rapid onset and are $\beta$-adrenergic blocking agents.

SUMMARY OF THE INVENTION

Heterocycle substituted-(3-loweralkylamino-2-$R_1$O-propoxy) pyridines and their pharmaceutically acceptable salts which have rapid onset anti-hypertensive effect.

DESCRIPTION OF THE PREFERRED EMBODIMENTS

An embodiment of the present invention is compounds having the formula

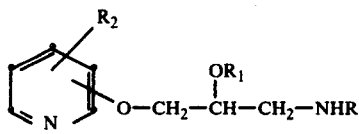

I wherein
R is $C_3$-$C_4$ branched alkyl,
$R_1$ is H or

wherein L is selected from $C_1$-$C_{10}$ alkyl, phenyl and substituted phenyl having up to two substituents which are independently selected from $C_1$-$C_4$ alkoxy, halo and $C_1$-$C_4$ alkyl and
$R_2$ is pyrrolyl, $C_1C_3$-alkylsubstituted pyrrolyl, carbocyclicarylsubstituted pyrrolyl, 1,3,4-oxadiazolyl $C_1$-$C_3$ alkyl substituted 1,3,4-oxadiazolyl, or carbocyclicarylsubstituted-1,3,4-oxadiazolyl, and pharmaceutically acceptable salts thereof.

$C_1$-$C_4$ alkyl includes linear and branched hydrocarbon alkyl such as methyl, sec. butyl, ethyl, —C(CH$_3$)$_3$ and the like. The L group includes $C_1$-$C_{10}$ linear and branched hydrocarbon alkyl such as methyl, n-decyl, tert. butyl, isoamyl, n-heptyl and the like with $C_1$-$C_4$ alkyl being preferred, and mono- and disubstituted phenyl such as 4-tert. butylphenyl, 2,6-dibromophenyl, 3-methylphenyl, 4-n-propylphenyl, 3,4-dimethoxyphenyl, 4-iodophenyl, 2-methyl-4-chlorophenyl, 4-fluorophenyl and the like with monosubstituted phenyl preferred. R is isopropyl, sec. butyl or tert. butyl being preferred.

The $R_2$ substituent includes the unsubstituted pyrrolyl and 2-(1,3,4-oxadiazolyl) groups and their $C_1$-$C_3$ alkyl or carbocyclicaryl substituted moieties. The carbocyclicaryl substituents include phenyl and the substitute phenyl groups as defined above for L. Examples of the substituted moieties are 3-methylpyrrolyl, 2,5-diisopropylpyrrolyl, 2,5-di-p-tolylpyrrolyl, 2-phehylpyrrolyl, 3-chlorophenylpyrrolyl, 5-ethyl-1,3,4-oxadiazolyl, 5-dibromophenyl-1,3,4-oxadiazolyl and the like.

The relative positions of the $R_2$ and —O—CH$_2$—CH(OR$_1$)—CH$_2$—NHR substituents in the Formula 1 pyridine may be varied and all these variations are included. Thus the —O—CH$_2$—CH(OR$_1$)—CH$_2$—NHR group may be in the 2, 3, or 4 position in the pyridine ring while the $R_2$ may be in any other open position. Examples of these various isomers are 4-[—O—CH$_2$—CH(OH)—CH$_2$—NH isopropyl]-3-(1-pyrrolyl)-pyridine,
4-[—O—CH$_2$—CH(OH)—CH$_2$NH sec. butyl]-3-(1,3,4-oxadiazol-2-yl) pyridine,
4-[O—CH$_2$—CH(OR$_1$)CH$_2$—NH tert. butyl]-2-(1-pyrrolyl) pyridine,
3-[O—CH$_2$—CH(OH)—CH$_2$NHR]-5-(2-ethylpyrrol-1-yl)pyridine,
3-[—O—CH$_2$—CH(OR$_1$)—CH$_2$—NHR]-5-(5-methyl-1,3,4-oxadiazol-2-yl)pyridine,
3-[O—CH$_2$—CH(OH)—CH$_2$—NHR]-6-(1-pyrrolyl)-pyridine,
3-[O—CH$_2$—CH(OH)—CH$_2$—NHR]-5-(2,5-diisopropyl pyrrol-1-yl)pyridine,
and the like.

Preferred compounds are those having the formula

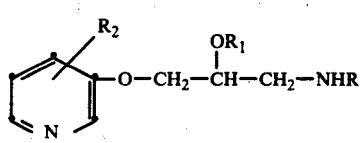

II with those Formula II compounds where $R_2$ is in the 2 position being especially preferred.

Another class of preferred compounds are those where —O—CH$_2$—CH(OR$_1$)—CH$_2$—NHR is in the two position. These compounds have the formula

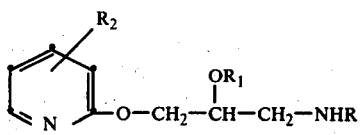

III

The compounds of Formula III where $R_2$ is in the 3,4, or 6 positions are more preferred and where $R_2$ is in the 3 or 4 position, the compounds are especially preferred.

The most preferred compounds of Formula III are those wherein $R_2$ is in the 3 position as illustrated by the following formula

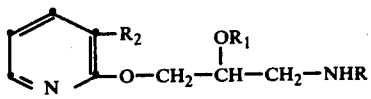

Examples of the most preferred compounds of Formula IV are 2-(3-sec. butylamino-2-hydroxypropoxy)-3-(1-pyrrolyl) pyridine,
2-(3-isopropylamino-2-hydroxypropoxy)-3-(2,5-di-n-propyl-pyrrol-1-yl)pyridine,
2-(3-tert. butylamino-2-acetyloxypropoxy)-3-(1-pyrrolyl)-pyridine,
2-(3-isopropylamino-2-benzoyloxypropoxy)-3-(2-methylpyrrol-1-yl)pyridine,
2-[3-sec. butylamino-2-(p-chlorobenzoyloxy)propoxy]-3-(1-pyrrolyl)pyridine,
2-(3-tert. butylamino-2-hydroxypropoxy)-3-(1,3,4-oxadiazol-2-yl)pyridine,
2-(3-isopropylamino-2-undecanoyloxypropoxy)-3-(5-phenyl-1,3,4-oxadiazol-2-yl)pyridine,
2-[3-tert. butylamino-2-(p-methoxybenzoyloxy)-propoxy]-3-(1,3,4-oxadiazol-2-yl)pyridine,
2-[3-isopropylamino- -hydroxypropoxy]-3-(5-methyl-1,3,4-oxadiazol-2-yl)pyridine,
2-[3-isopropylamino-2-(2-bromo-4-methylbenzoyloxy) propoxy]-3-(1,3,4-oxadiazol-2-yl)pyridine,
2-[3-tert. butylamino-2-(3,5-dimethoxybenzoyloxy)-propoxy]-3-(1-pyrrolyl)pyridine,
2-(3-sec. butylamino-2-hydroxypropoxy)-3-(5-methyl-1,3,4-oxadiazol-2-yl)pyridine,
2-(3-isopropylamino-2-octanoyloxypropoxy)-3-(1-pyrrolyl)pyridine,
2-(3-tert. butylamino-2-isovaleryloxypropoxy)-3-(1-pyrrolyl)pyridine
and the like.

Preferred compounds of Formula I-IV are those wherein $R_1$ is hydrogen. More preferred are Formula I-IV compounds where $R_1$ is hydrogen and R is tert. butyl. Most preferred compounds are the compounds of Formula IV where $R_1$ is H, $R_2$ is 1-pyrrolyl or substituted 1-pyrrolyl and R is tert. butyl.

The substituted pyridines of the present invention include all the optical isomer forms, that is mixtures of enantiomers e.g. racemates as well as the individual enantiomers. These individual enantiomers are commonly designated according to the optical rotation they effect, by (+) and (−), (L) and (D), (l) and (d) or combinations of these symbols. The symbols (S) and (R) stand for sinister and rectus respectively and designate an absolute spatial configuration of the enantiomer.

The pyridines of the present invention can be prepared by any convenient process.

One such process involves the coupling of a hydroxy or halopyridine with a suitable substituted oxazolidine and hydrolyzing the reaction product obtained. This process is illustrated by the following set of reaction equations:

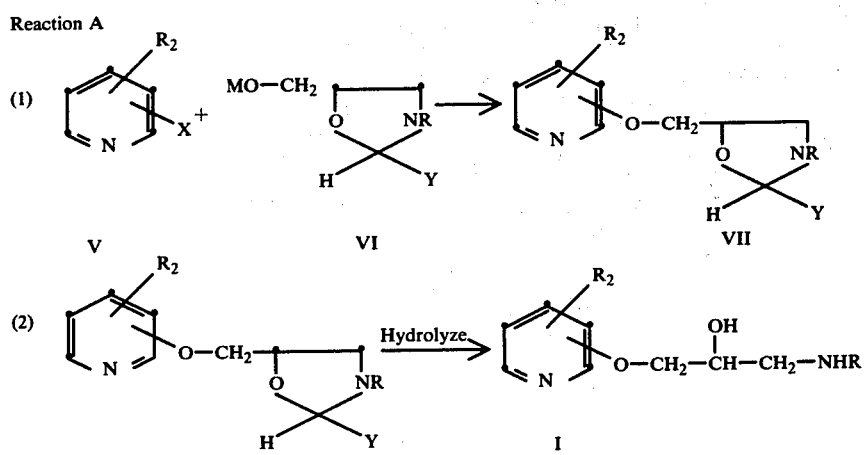

X may be Cl, Br, I, with Cl being preferred, or hydroxy. When X is Cl, Br or I, M is an alkali metal, either potassium or sodium. When X is hydroxy, M is aryl or alkylsulfonyl. Y can be hydrogen or the residue of any suitable aldehyde

e.g. an arylaldehyde such as benzaldehyde, naphthaldehyde and the like, or an alkanal such as acetaldehyde, butyraldehyde and the like. The process for preparing oxazolidines where M is hydrogen or said sulfonyl group is disclosed in U.S. Pat. Nos. 3,718,637 and 3,657,237 and to the extent necessary the pertinent disclosure is incorporated herein by reference. The alkali metal salt of the oxazolidine is prepared in a conventional manner by reaction of the corresponding hydroxymethyloxazolidine with an appropriate amount of an alkali base reactant. However, this Reaction A may also be carried out with in-situ formation of the alkali metal oxazolidine salt (Formula VI) by reacting the oxazolidine

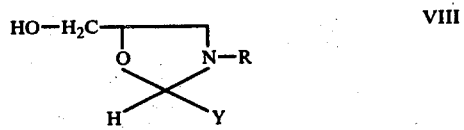

with the Formula V pyridine in the presence of a strong base such as an alkali metal alkoxide (e.g. K-O-C-$(CH_3)_3$) or sodium hydride.

The coupling reaction can be carried out at temperatures ranging from about 0° C. to the solvent reflux temperature. A temperature range of about 10° C. to about 75° C. is preferred. The reaction is generally carried out in a solvent. Any suitable solvent may be used. Examples of useful solvents are dimethylformamide, dimethylsulfoxide, hexamethylphosphoramide, tert. butanol, alkanols and the like. The hydrolysis is carried out using conventional acid hydrolysis reagent and techniques e.g. treatment with acetic acid or a solution of any strong mineral acid such as HCl or $H_2SO_4$. The hydrolysis product can be directly obtained as the salt of the acid used for the hydrolysis. Ordinarily, the product I is recovered as the free base after conventional neutralization of the salt.

The coupling reaction is ordinarily carried out at atmospheric pressure. Higher pressures may be used if desired.

When a racemic oxazolidine (Formula VI or VIII) is used as a reactant, the product is obtained as a racemate. The racemate may be separated into its individual enantiomers by conventional resolution techniques.

When Y in the oxazolidine (Formula VI or VIII) is other than hydrogen, in addition to the chiral center at oxazolidine position 5 there is a second chiral center at position 2. However, whenever the oxazolidine is designated e.g. as (S), (R) or (R,S), the designation refers only to the optical configuration around the carbon atom at the 5 position.

By using a single optical isomer of said oxazolidine in the above reactions, the product may be obtained directly as a single enantiomer. Thus, if the S-isomer of the oxazolidine is used, then the product obtained will be the S-iomer. This provides a convenient way for directly preparing individual isomers of the present pyridines.

The intermediate of Formula V where $R_2$ is pyrrolyl is prepared by the conventional reaction of a halo or hydroxy substituted aminopyridine with a suitable diketo compound or a labile equivalent such as an acetal or ketal in the presence of a suitable condensation agent as illustrated by the following equation:

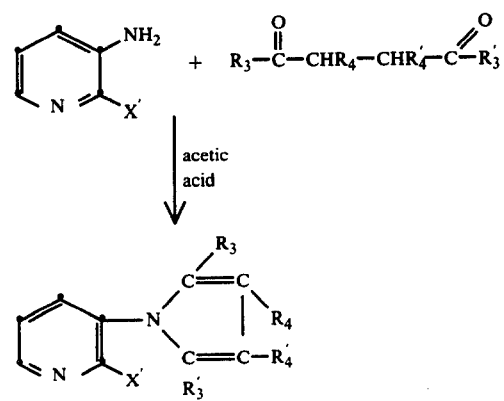

wherein X' is Br, Cl or OH, $R_3$ or $R_3'$ is H or $C_1$-$C_3$ alkyl and $R_4$ or $R_4'$ is H or $C_1$-$C_3$ alkyl.

The intermediate of Formula V where $R_2$ is 1,3,4-oxadiazole group is prepared by the conventional acylation of a nicotinoyl hydrazine N-oxide followed by simultaneous cyclization of the diacyl hydrazine product and halogenation of the pyridine ring as illustrated by the following equations

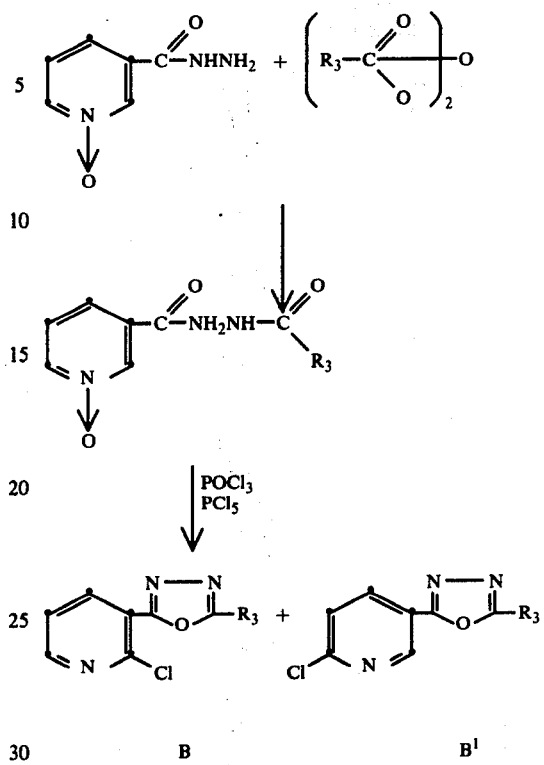

Conventional reaction conditions and reagents are employed. The isomeric products B and $B^1$, are separated using available procedures e.g. chromatography.

Pyridines of the present invention wherein $R_1$ is other than hydrogen are conveniently prepared by treating the corresponding pyridine where $R_1$ is hydrogen with an appropriate acylating agent such as an acyl halide, e.g. undecanoyl chloride, pivaloyl chloride, benzoyl-chloride, p-methoxybenzoyl chloride, an anhydride e.g. acetic anhydride, and the like. The reaction is illustrated by the following equations:

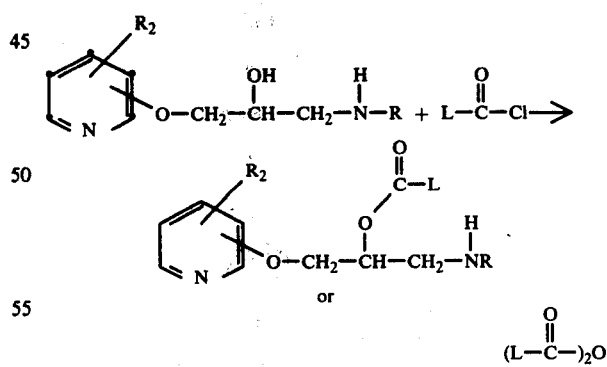

The compounds of the present invention also include the pharmaceutically acceptable salts of the novel pyridines. These salts are generally salts of the Formula I pyridines and organic or inorganic acids. These salts are prepared by treating the pyridine with an appropriate amount of a useful acid, generally in a suitable solvent. Examples of useful organic acids are isethionic acid and carboxylic acids such as maleic acid, acetic acid, tartaric acid, propionic acid, fumaric acid, succinic acid, pamoic acid, oxalic acid, pivalic acid and the like; useful inorganic acids are hydrohalo acids such as HCl, HBr, HI; sulfuric acid, phosphoric acid and the like. The hydrochloride and hydrogen maleate salts are examples of preferred salts.

The compounds of the present invention have anti-hypertensive activity of rapid onset and are also β-adrenergic blocking agents. This anti-hypertensive activity is believed to be the result of peripheral vasodilation via a mechanism not directly related to β-adrenergic blockade. One advantage of the present pyridines have over ordinary β-adrenergic agents is that the anti-hypertensive effect is immediate and generally of extended duration.

This rapid onset anti-hypertensive activity is determined by administering a representative pyridine of the present invention to spontaneously hypertensive (SH) rat and measuring the effect on blood pressure. An example of a representative compound having this anti-hypertensive activity is (S)-3-(1-pyrrolyl)-2-(3-tert. butylamino-2-hydroxypropoxy)pyridine.

The β-adrenergic blocking activity of the present pyridines is determined by measuring the ability of a representative pyridine to block isoproterenol induced β-adrenergic stimulant effects such as heart rate increase, hypotension and bronchodilation, in animals.

The ability of the present pyridines to reduce blood pressure, in an SH rat, rapidly and for extended duration, indicates that the present pyridines and their salts are useful to treat hypertension in humans. Likewise, the observed β-adrenergic blocking activity of these pyridines indicates that they are useful in humans as β-adrenergic blocking agents.

For use as anti-hypertensives and/or β-adrenergic blocking agents, the compounds of the present invention can be administered orally, by inhalation, by suppository or parenterally i.e. intravenously, intraperitoneally etc. and in any suitable dosage form. The compounds may be offered in a form (1) for oral administration e.g. as tablets in combination with other compounding ingredients (diluents or carriers) customarily used such as talc, vegetable oils, polyols, benzyl alcohols, starches, gelatin and the like — or dissolved, dispersed or emulsified in a suitable liquid carrier — or in capsules or encapsulated in a suitable encapsulating material; or (2) for parenteral administration, dissolved, dispersed, or emulsified in a suitable liquid carrier or diluent or (3) as an aerosol or (4) as a suppository. The compounds may also be used in delayed release or metered release dosage forms. The ratio of active ingredient (present pyridine) to compounding ingredients will vary as the dosage form requires. Conventional procedures are used to prepare the pharmaceutical formulations.

The dosage level for the present compounds may be varied from about 0.01 mg. to about 50 mg. per kilogram of animal body weight per day. Daily doses ranging from about 0.04 to about 2.5 mg/kg are preferred, with about 0.08 to about 1.25 mg/kg being a more preferred range. Oral administration is preferred. Either single or multiple daily doses may be administered depending on unit dosage.

Thus, another embodiment of this invention is a pharmaceutical composition containing an anti-hypertensive and/or β-adrenergic blocking amount of a compound of the present invention.

The following examples illustrate the preparation of representative examples of the present pyridines. Where no isomer designation is indicated, the product is the racemate. All temperatures are in degrees Celcius.

EXAMPLE 1

Preparation of (S) 3-(1-pyrrolyl)-2-(3-tert butylamino-2-hydroxypropoxy)pyridine hydrogen maleate salt a. A solution of acetic acid (25 ml), 2-chloro-3-aminopyridine (5.1 g, 0.04 m) and 2,5-dimethoxytetrahydrofuran (0.05 m) was heated to reflux. After two hours, the mixture was concentrated to dryness, treated with ice and neutralized with saturate $Na_2CO_3$ solution. The aqueous layer was extracted with $CHCl_3$ ($3 \times 100$ ml). The organic extract was dried over $Na_2SO_4$, filtered and concentrated to dryness. The residue was distilled to yield 5.3 g (75% yield) of 2-chloro-3-(1-pyrrolyl) pyridine; b.p=95°–100° at 0.5 mm.

b. A dry flask was charged, under nitrogen, with tert. butanol (25 ml.), potassium metal (0.39 g; 0.01 m) and (S) 2-phenyl-3-tert butyl-5-hydroxymethyloxazolidine (2.5 ml) and heated at 40° with stirring until the potassium reacted. Then, 2-chloro-3-(1-pyrrolyl)pyridine (1.65g; 0.009 m) in tert butanol (5 ml) was added and the mixture heated at 70°. After 15 hours, the mixture was concentrated to dryness and stirred with water (150 ml) and acetic acid (9.0 g). After 5 hours, the solution was extracted with diethyl ether ($2 \times 100$ ml). The aqueous layer was neutralized with saturated $Na_2CO_3$ solution and extracted with chloroform ($3 \times 100$ ml). The organic layer was dried over $Na_2SO_4$, filtered and concentrated to dryness. The residue was crystallized with maleic acid in isopropanol to yield 1.8 g (49% yield) of 3-(1-pyrrolyl)-2-(3-tert butylamino-2-hydroxypropoxy)-pyridine hydrogen maleate salt, m.p. = 122°–125°.

EXAMPLE 2

Preparation of (S) 3 (and 5)-[2-(5-methyl-1,3,4-oxadiazolyl]-2-(3-tert butylamino-2-hydroxypropoxy)pyridine hydrogen maleate salt a. A mixture of nicotinoyl hydrazine-N-oxide (25.3 g; 0.166 m), acetic acid (85 ml) and acetic anhydride (16.9 g; 0.166 m) was heated at reflux. After one hour, the reaction mixture was cooled and poured into diethylether to yield 32 g of N-acetylnicotinoylhydrazine N-oxide.

b. A solution of N-acetylnicotinoylhydrazine-N-oxide (30 g; 0.15 m), $POCl_3$ (120 ml) and $PCl_5$ (42 g; 0.2 m) was heated at reflux. After one and one-half hours, the mixture was concentrated to dryness. The residue was treated with ice and the product extracted with $(C_2H_5)_2O$ ($4 \times 100$ ml). The combined organic extract was dried over $Na_2SO_4$, filtered and concentrated to dryness. The residue was chromatographed on silica gel and the product eluted with $CHCl_3$ to yield 4.3 g (14% yield) of 2-chloro-3-[2-(5-methyl-1,3,4-oxadiazolyl)-]pyridine m.p. 127–129° C. and 2.3 g (8% yield) of 2-chloro-5-]2-(5-methyl-1,3,4-oxadiazolyl)]pyridine, m.p. 147°148°.

c. A 36% yield of (S) 3-[2-(5-methyl-1,3,4-oxadiazolyl)]-2-(3-tert butylamino-2-hydroxypropoxy)-pyridine hydrogen maleate, m.p. = 127°–128°, was obtained by substituting 2-chloro-3-[2-(5-methyl-1,3,4-oxadiazolyl)]pyridine for the 2-chloro-3-(1-pyrrolyl) pyridine and carrying out the reaction substantially as described in Example 1, step b.

d. A 24% yield of (S) 5-[2-(5-methyl-1,3,4-oxadiazolyl)]-2-(3-tert butylamino-2-hydroxypropoxy)-pyridine hydrogen maleate, m.p. = 155°-156° was obtained by substituting 2-chloro-5-[2-(5-methyl-1,3,4-oxadiazolyl)]-pyridine for the 2-chloro-3-(1-pyrrolyl)-pyridine and carrying out the reaction substantially as described in Example 1, step b.

EXAMPLE 3

Preparation of (S) 3-(3-tert butylamino-2-hydroxypropoxy)-2-[2-(5-methyl-1,3,4-oxadiazolyl)]pyridine a. To a solution of (S) 2-phenyl-3-tert butyl-5-hydroxymethyloxazolidine (2.5 g, .011 m) and dry pyridine (5 ml) is added portionwise p-toluenesulfonyl chloride (2.0 g; 0.011 m) while maintaining the temperature of the reaction below 30°. After the addition, the mixture is stirred at room temperature for 3 hours. To the solid mixture is added a solution of $K_2CO_3$ (1.45 g; 0.01 m) in $H_2O$ (10 ml) and the solution extracted with chloroform (3×25 ml). The organic layer is dried over $Na_2SO_4$, filtered and concentrated to dryness below 50° to yield the tosylate of (S) 2-phenyl-3-tert butyl-5-hydroxymethyloxazolidine which is used in the next step without further purification.

b. Into a dry flask under $N_2$ is added 3-hydroxy-2-[2-(5-methyl-1,3,4-oxadiazolyl)]pyridine (1.5, .01 m), DMF (20 ml) and NaH (50% mineral oil, .5 g, .01 m). After stirring at room temperature for 15 min., the tosylate from step a. (0.01 m) in DMF (20 ml) is added and the solution heated under reflux with stirring. After 12 hours, the solvent is removed under reduced pressure to (1-5 mm). The residue is treated with 1N HCl (100 ml) and heated on a stream bath for ¾ hour. After cooling, the aqueous layer is extracted with $Et_2O$ (2×50 ml), neutralized with saturated $Na_2CO_3$ and extracted with $CHCl_3$ (3×100 ml). The organic layer is dried over $Na_2SO_4$, filtered and concentrated to dryness to yield (S) 3-(3-tert butylamino-2-hydroxypropoxy)-2-[2-(5-methyl-1,3,4-oxadiazolyl)]pyridine.

EXAMPLE 4

Preparation of (S) 2-(3-tert butylamino-2-hydroxypropoxy)-3-[1-(3,4-dimethylpyrrolyl)]pyridine hydrogen maleate a. A solution of 2-chloro-3-aminopyridine (12.9 g, 0.1 m) and thionyl chloride (5.5 g, 0.05 m) in $Et_2O$ (100 ml) is heated at reflux with stirring. After 15 hours, the 2-chloro-3-aminopyridine HCl is filtered off and the solution concentrated to dryness to yield 2-chloro-3-thionylaminopyridine (1).

b. A mixture of 1 (7.0 g, 0.05 m) and 3,4-dimethylbutadiene (4.5 g, 0.054 m) is heated at reflux with stirring. After 8 hours, the mixture is distilled to yield 2-[3-(2-chloropyridyl)]-3,6-dihydro-4,5-dimethyl-1,2-thiazin-1-oxide (2).

c. A solution of 2 (11.1 g, 0.05 m), KOH (11 g, 0.02 m) and EtOH (150 ml) is heated at reflux. After 1.5 hours, the mixture is poured into $H_2O$ (700 ml) and extracted with $Et_2O$ (3×400 ml). The organic extracts are dried over $Na_2SO_4$, filtered and concentrated to dryness to yield 2-chloro-3-[1-(3,4-dimethylpyrrolyl)]pyridine (3).

d. Treatment of the pyridine (3) with a suitable oxazolidine, as in Example 1 b., yields the corresponding 3-[1-(3,4-dimethylpyrrolyl)]-2-(3-tert butylamino-2-hydroxypropoxy)pyridine hydrogen maleate salt.

Using the processes substantially as described in Examples 1, 2, 3, or 4, the compounds having the following formulae are also prepared. β in the formulae represents the —$CH_2$—CHOH—$CH_2$—NHR group.

| Example | Formula |
|---|---|
| 5 | (S) structure |
| 6 | (R) structure |
| 7 | structure |
| 8 | (R,S) structure |
| 9 | structure |
| 10 | structure |
| 11 | structure |
| 12 | structure |
| 13 | structure |
| 14 | structure |

| Example | Formula |
|---------|---------|
| 15 | |
| 16 | |
| 17 | |
| 18 | |
| 19 | |

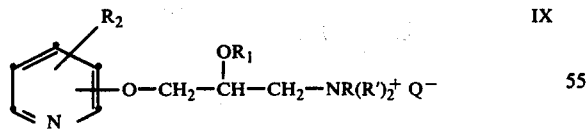

Isopropyl or sec butyl amino analogues of the compounds of the above examples are prepared by substituting suitable oxazolidines e.g. 2-phenyl-3-isopropyl-5-hydroxymethyloxazolidine, (R) 2-methyl-3-isopropyl-5-hydroxymethyloxazolidine, 3-sec butyl-5-hydroxymethyl-oxazolidine, for the (S) 2-phenyl-3-tert butyl-5-hydroxymethyloxazolidine reactant.

Similarly, the derivatives of the Example compounds where the 2-hydroxy group is acylated are prepared by treatment of the Example compound with a suitable reagent such as any acyl halide or anhydride to produce the corresponding ester derivative. For example, S3-(1-pyrrolyl)-2-(3-tert butylamino-2-hydroxypropoxy)-pyridine is treated with trimethylacetylchloride in a suitable solvent to obtain the corresponding S3-(1-pyrrolyl)-2-(3-tert butylamino-2-pivaloyloxypropoxy)pyridine.

The present invention also includes the quaternary ammonium salts having the formula:

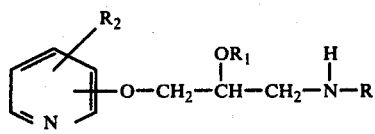   IX wherein R, $R_1$ and $R_2$ is defined above, R' is an alkyl (e.g. $C_1$-$C_4$ alkyl, benzyl and the like) group and Q is a halogen especially Cl, Br or I. These quaternary salts are prepared using any convenient method. For example, they can be prepared by treating the compound of Formula I with an alkyl halide such as methyliodide or benzylchloride to obtain the corresponding quaternary salt of Formula IX.

The N-pyridine oxides having the formula

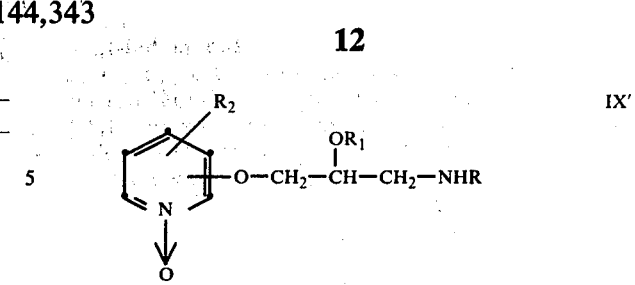   IX' with R, $R_1$ and $R_2$ as defined above, and include the acid addition salts and quaternary ammonium salts thereof. These N-oxides are also prepared using conventional reagents and procedures. For example, a convenient method of preparing these oxides is to treat the intermediate of Formula V with an oxidizing agent e.g. $H_2O_2$ using conventional reaction conditions to produce the oxidized intermediate having the formula

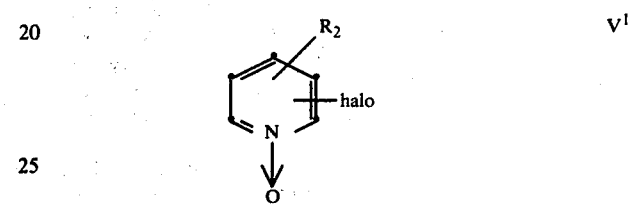   V¹

The formula $V^1$ compound is then substituted for the formula V compound in Reaction A above to obtain the pyridine-N-oxide of Formula IX'.

Claims to invention follow.

What is claimed is:

1. Compound having the formula

wherein
R is $C_3$-$C_4$ branched alkyl,
$R_1$ is H or $$-\underset{\underset{O}{\|}}{C}-L$$

wherein L is selected from $C_1$-$C_{10}$ alkyl, phenyl and substituted phenyl having up to two substituents independently selected from $C_1$-$C_4$ alkoxy, halo and $C_1$-$C_4$ alkyl and,
$R_2$ is 1-pyrrolyl, $C_1$-$C_3$ alkyl substituted-1-pyrrolyl, carbocyclicaryl substituted-1-pyrrolyl, 2-(1,3,4-oxadiazolyl), $C_1$-$C_3$ alkyl substituted 2-(1,3,4-oxadiazolyl) or carbocyclic substituted -2-(1,3,4-oxadiazolyl) and pharmaceutically acceptable salts thereof.

2. The compounds of claim 1 having the S-isomer configuration.

3. The compounds of claim 2 wherein $R_1$ is H.

4. The compounds of claim 3 wherein R is tert butyl.

5. The compounds of claim 1 wherein $R_2$ is said pyrrolyl or substituted pyrrolyl.

6. The compounds of claim 5 wherein $R_1$ is H and $R_2$ is tert butyl.

7. The compounds of claim 6 wherein $R_2$ is 1-pyrrolyl.

8. The compounds of claim 7 having the S-isomer configuration.

9. The compounds of claim 1 wherein $R_2$ is said 2-(1,3,4-oxadiazolyl) or substituted 2-(1,3,4-oxadiazolyl).

10. The compounds of claim 9 wherein $R_1$ is H and $R_2$ is tert butyl.

11. The compounds of claim 10 having the S-isomer configuration.

12. A pharmaceutical composition useful for treating hypertension containing an effective amount of a compound of claim 1.

13. Compound having the formula

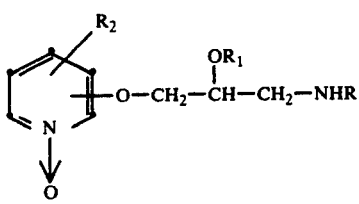

wherein R, $R_1$ and $R_2$ are defined as in claim 1 and pharmaceutically acceptable salts and quaternary ammonium salts thereof.

14. Compound having the formula

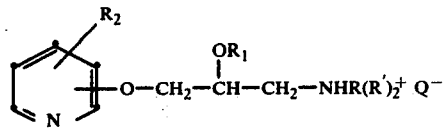

wherein R, $R_1$ and $R_2$ are defined as in claim 1, R' is alkyl and Q is halogen.

15. Compound of claim 5 selected from 3-(1-pyrrolyl)-2-(3-tert butylamino-2-hydroxypropoxy)-pyridine and 2-(3-tert butylamino-2-hydroxypropoxy)-3-[1-(3,4-dimethylpyrrolyl)] pyridine.

16. A compound of claim 15 selected from (S) 3-(1-pyrrolyl)-2-(3-tert butylamino-2-hydroxypropoxy) pyridine and the hydrogen maleate salt thereof.

17. A compound of claim 15 selected from (S) 2-(3-tert butylamino-2-hydroxypropoxy)-3-[1-(3,4-dimethyl pyrrolyl)] pyridine and the hydrogen maleate salt thereof.

18. Compound of claim 11 selected from (A.) (S) 3-[2-(5-methyl-1,3,4-oxadiazolyl)]-2-(3-tert-butylamino-2-hydroxypropoxy) pyridine, (B.) (S) 5-[2-(5-methyl-1,3,4-oxadiazolyl)]-2-(3-tert butylamino-2-hydroxypropoxy) pyridine and (C.) (S) 3-(3-tert butylamino-2-hydroxypropoxy)-2-[2-(5-methyl-1,3,4-oxadiazolyl)] pyridine.

19. The hydrogen maleate salt of compound A.) or B.) of claim 18.

* * * * *